US00PP31455P2

(12) United States Plant Patent
Korlipara

(10) Patent No.: US PP31,455 P2
(45) Date of Patent: Feb. 18, 2020

(54) ***LEUCANTHEMUM* PLANT NAMED 'LEMON PUFF'**

(50) Latin Name: ***Leucanthemum* x *superbum***
Varietal Denomination: Lemon Puff

(71) Applicant: Terra Nova Nurseries, Inc., Canby, OR (US)

(72) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 16/350,962

(22) Filed: Feb. 4, 2019

(51) Int. Cl.
*A01H 5/02* (2018.01)
*A01H 6/14* (2018.01)

(52) U.S. Cl.
USPC ..... Plt./285

(58) Field of Classification Search
USPC ..... Plt./285
See application file for complete search history.

*Primary Examiner* — Susan McCormick Ewoldt
(74) *Attorney, Agent, or Firm* — Klarquist Sparkman, LLP

(57) ABSTRACT

A new and distinct *Leucanthemum* plant named 'Lemon Puff' characterized by double daisy type inflorescences, yellow inflorescence buds and young ray florets, fully open inflorescences that are medium sized and display numerous white and yellow ray florets around a gold disc, ray florets that are obelliptic to linear with mildly lacerated tips giving a more fluffy appearance to the inflorescence, excellent bloom number, a low, compact habit, and excellent vigor.

1 Drawing Sheet

Botanical denomination: *Leucanthemum* x *superbum*.
Variety designation: 'Lemon Puff'.

BACKGROUND OF THE INVENTION

The present invention relates to a new and distinct cultivar of *Leucanthemum* given the cultivar name 'Lemon Puff'. *Leucanthemum* is in the family Asteraceae. The exact parents for this cross are unknown; the new cultivar originated from a controlled cross between unnamed, proprietary *Leucanthemum* x *superbum* seedlings.

Compared to *Leucanthemum* 'Bridal Bouquet', U.S. Plant Pat. No. 24,260, the new cultivar is more double, and has shorter ray florets and a taller habit.

Compared to *Leucanthemum* 'Macaroon', U.S. Plant Pat. No. 26,905, the new cultivar is taller and has smaller flowers.

Compared to *Leucanthemum* 'Victorian Secret', U.S. Plant Pat. No. 22,654, the new cultivar has smaller flowers.

SUMMARY OF THE INVENTION

This new *Leucanthemum* cultivar is uniquely distinguished by:

1. double daisy type inflorescences,
2. yellow inflorescence buds and young ray florets,
3. fully open inflorescences that are medium sized and display numerous white and yellow ray florets around a gold disc,
4. ray florets that are obelliptic to linear with mildly lacerated tips giving a more fluffy appearance to the inflorescence,
5. excellent bloom number,
6. a low, compact habit, and
7. excellent vigor.

This new cultivar has been reproduced only by asexual propagation (division and tissue culture). Each of the progeny exhibits identical characteristics to the original plant.

Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a one-year-old plant growing in the ground in full sun in the trial field in mid-June in Canby, Oreg.

FIG. 2 shows a two-year-old plant growing in the ground in full sun in the trial field in early June in Canby, Oreg.

DETAILED PLANT DESCRIPTION

The following is a detailed description of the new *Leucanthemum* cultivar based on observations of 3-year-old specimens growing in the field in full sun under typical outdoor conditions in Canby, Oreg. Canby is in Zone 8 on the USDA Hardiness map. Temperatures range from a high of 95° F. in August to an average of 32° F. in January. Normal rainfall in Canby is 42.8 inches per year in the trial fields in Canby, Oreg. The color descriptions are all based on *The Royal Horticultural Society Colour Chart, 5th* edition, 2007.

Plant:

*Type*.—Herbaceous perennial.
*Hardiness*.—USDA Zones 5 to 9.
*Size*.—56 cm wide and 46 cm tall to top of inflorescences.
*Form*.—Basal clump.
*Number of stems*.—About 120.
*Vigor*.—Excellent.

Stem (flowering):

*Type*.—Ascending strongly upright, thick.

*Number of stems*.—About 120 stems from the crown, each flowering with 1 inflorescence per stem.

*Size*.—Grows to about 43.5 cm tall to a terminal inflorescence and 6 cm wide at base.

*Number of leaves per stem*.—Up to 24, with oldest leaves senescent.

*Stem strength*.—Strong.

*Internode length*.—1 cm to 3 cm.

*Surface texture*.—Pubescent.

*Color*.—Green 137A.

Leaves:

*Type*.—Simple.

*Shape*.—Lanceolate.

*Arrangement*.—Alternate.

*Blade size*.—Grows to 9.4 cm long and 2 cm wide.

*Margins*.—Coarsely serrate.

*Apex*.—Acute.

*Base*.—Clasping.

*Surface texture*.—Pubescent on both sides.

*Venation*.—Pinnate.

*Petiole*.—Sessile.

*Color*.—Topside Green 137A with main vein Yellow Green 147C, bottom side Yellow Green 147B with main vein Yellow Green 147D.

Inflorescence:

*Type*.—Composite on terminal stalked heads.

*Number of inflorescences per plant*.—About 120.

*Flower density*.—Dense.

*Size*.—Grows to 4.5 cm wide and 2 cm deep.

*Form*.—Ray florets held upright when young, lower ray florets reflex down with maturity, mature disc is mostly flat.

*Bud* (*immature inflorescence*).—1.7 cm wide and 1 cm deep, ray florets held upwards and inner rays cupped inwards, Yellow 9C.

*Ray florets*.—With 1 pistil and no stamen, about 160 in number, 2 cm long and 0.5 mm to 17 mm wide, variably 3 to 5 cleft; lobes obelliptic to linear, tip retuse, margins entire, base attenuate, glabrous on both sides; top and bottom side Yellow 9C when young changing to White NN155B; claw to 2.5 mm long and 0.5 mm wide, Yellow Green 144B; pistil 3 mm long, ovary 1 mm long, Yellow Green 145D, style 1 mm long, Yellow Green 145D, 2 branched stigma 0.5 mm long, Yellow 13A.

*Disc*.—Slightly conic becoming flat, becoming 10 mm deep and 20 mm wide with maturity, Yellow Orange 15A.

*Disc florets*.—About 300 in number, each 5 mm long and 1 mm wide; corolla tubular campanulate, 4 mm long and 1 mm wide, 5 lobed, glabrous, Yellow 17B on top half and Yellow Green 145A on the bottom half; pistil 1, 7 mm long, ovary 1 mm long and Yellow Green 145D, style 2 mm long, Greyed Yellow 160B, 2 branched stigma 0.5 mm long, Greyed Yellow 160B; stamen 5 in number, 4 mm long, filaments 1 mm long, Yellow Green 150D, anthers 3 mm Yellow Orange 17A, pollen none.

*Involucral bracts*.—About 30 in number, in 3 imbricate whorls, area 2.9 cm wide and 10 mm deep, lobes lanceolate to ovate in shape, grow to 9 mm long and 6 mm wide, Green 137A, margin thin and somewhat transparent, Greyed Purple 187A, tip acute, glabrous.

*Receptacle*.—Grows to 18 mm wide and 4 mm deep, Yellow Green 145C.

*Bloom period*.—June through July in Canby, Oreg.

*Fragrance*.—Slight to none.

*Lastingness*.—Each inflorescence lasts about three weeks in Canby, Oreg.

Seeds: None seen.

*Fertility*.—Low.

Disease and pests: The new cultivar is typical to the genus. No known resistances to pests or diseases. No problems have been found in Canby, Oreg.

I claim:

1. A new and distinct *Leucanthemum* plant as herein illustrated and described.

* * * * *

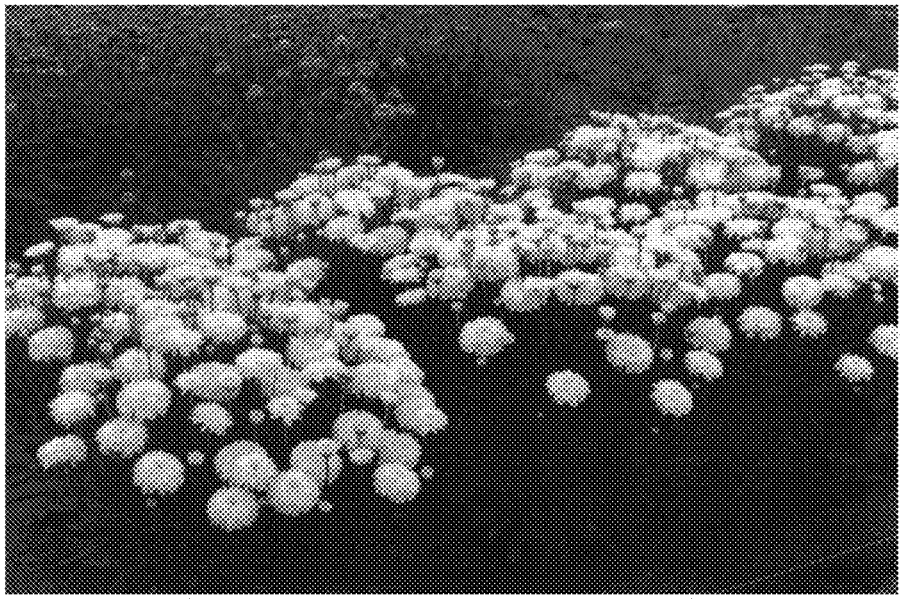

Fig.1 Below
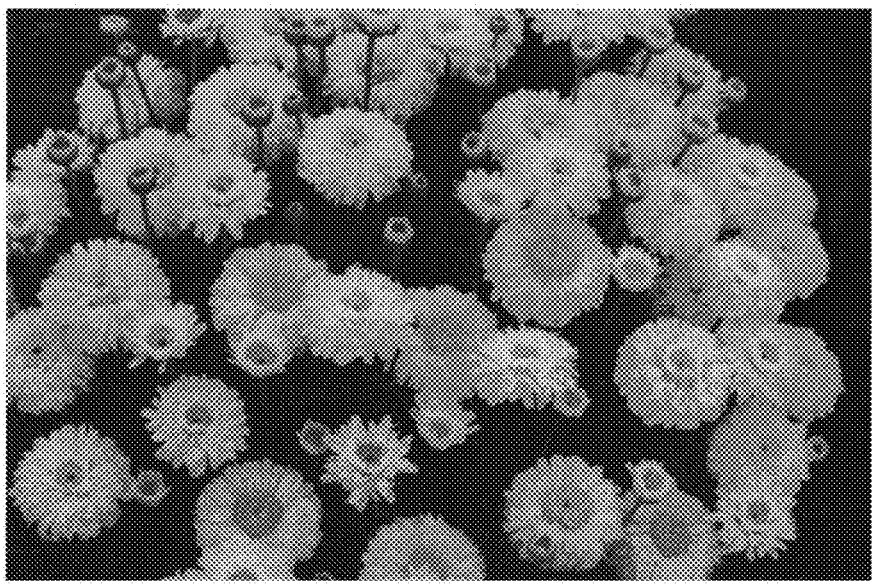
Fig. 2 Below